United States Patent [19]
Park et al.

[11] Patent Number: 5,627,171
[45] Date of Patent: May 6, 1997

[54] SPHINGOSINE-1-PHOSPHATE/ TRIMETHYLSPHINGOSINE COMPOSITION

[75] Inventors: Yong S. Park; Yasuyuki Igarashi; Sen-itiroh Hakomori, all of Seattle, Wash.

[73] Assignee: Oncomembrane, Inc., Seattle, Wash.

[21] Appl. No.: 225,796

[22] Filed: Apr. 11, 1994

[51] Int. Cl.$^6$ .......................... A61K 31/66; A61K 31/14; A61K 9/127
[52] U.S. Cl. .................... 514/114; 514/642; 424/450
[58] Field of Search ............................... 514/114, 642; 424/450

[56] References Cited

U.S. PATENT DOCUMENTS

| 5,151,360 | 9/1992 | Handa et al. | 435/240.2 |
| 5,260,288 | 11/1993 | Igarashi et al. | 514/114 |

Primary Examiner—Jerome D. Goldberg
Attorney, Agent, or Firm—Sughrue, Mion, Zinn, Macpeak & Seas

[57] ABSTRACT

Sphingosine-1-phosphate/N,N,N-trimethylsphingosine composition to modulate cell growth.

5 Claims, 9 Drawing Sheets

SCHEME IV SYNTHESIS OF 3 & 4

SCHEME V SYNTHESIS OF 5F-TMS AND 4-ALKYN-TMS

SPHINGOSINE-1-PHOSPHATE/ TRIMETHYLSPHINGOSINE COMPOSITION

FIELD OF THE INVENTION

The instant invention relates to compositions comprising sphingosine-1-phosphate (Sph-1-P), or derivatives thereof, and N,N,N-trimethylsphingosine (TMS), or derivatives thereof, to inhibit cell motility and cell proliferation.

BACKGROUND OF THE INVENTION

Trimethylsphingosine, and derivatives thereof, have specific activities on cells. TMS, for example, inhibits cell proliferation, inhibits protein kinase C (PKC), inhibits cell migration, inhibits platelet activation, inhibits $O_2-$ production by cells, and modulates expression of cell surface molecules, such as selectins. U.S. Pat. Nos. 5,137,919, 5,151,360 and 5,248,824, herein incorporated by reference, teach TMS, methods of making same and methods of using same.

Sphingosine-1-phosphate, and derivatives thereof, have a different effect on cells, namely, inhibiting cell motility. Sph-1-P does not affect PKC but inhibits motility through actin filament reorganization. U.S. Pat. No. 5,260,288, herein incorporated by reference, teaches Sph-1-P, methods of making same and methods of using same.

SUMMARY OF THE INVENTION

Accordingly, an object of the instant invention is to provide compositions of N,N,N-trimethylsphingosine, and derivatives thereof, and sphingosine-1-phosphate, and derivatives thereof, that demonstrate synergism in potentiation of TMS activity, particularly with respect to antimetastatic properties of tumor cells and the uncontrolled growth of same.

That and other objects have been achieved in the realization that combination of TMS, or derivatives thereof, and Sph-1-P, or derivatives thereof, results in greater activity than either TMS or Sph-1-P alone or what might be expected when the activities of each are added together. the synergistic effect of the two active agents arises from the complimentary activities of same. TMS acts in a PKC-dependent fashion whereas Sph-1-P acts in a PKC-independent fashion.

BRIEF DESCRIPTION OF THE DRAWINGS

FIG. 4 sets forth the scheme for making one of the intermediate structures.

FIG. 5 depicts a scheme which uses the intermediate 3a a of FIG. 4 to make another intermediate, structure 6b.

FIG. 6 depicts a scheme using structure 6b to make the target compounds.

DETAILED DESCRIPTION OF THE INVENTION

Figure 1:
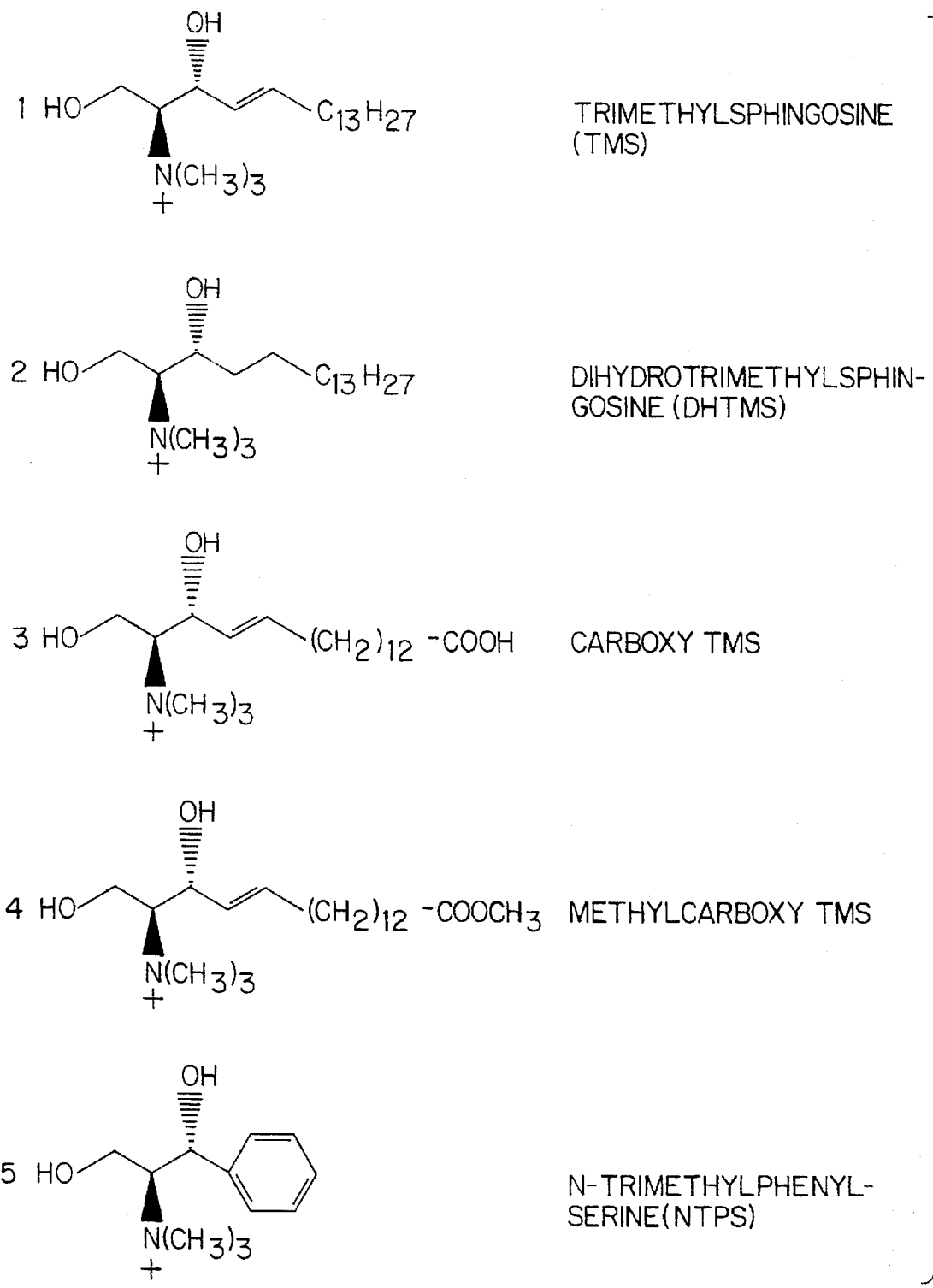
FIG. 1 depicts trimethylsphingosine and several derivatives thereof.

For the purposes of the instant invention, "derivatives" are considered equivalents of the parent compound. A derivative is a parent compound modified, for example, structurally, such as, by conjugation to another molecule, such as, polyethylene glycol, by halogenation, olefination, hydroxylation, hydration, carboxylation, truncation and the like, so long as the desired activities of the parent compound are realized. The desired activities possessed by a derivative may be reduced in level as compared to the parent compound. A derivative may have enhanced desired activities or alternative properties not found in the parent compounds.

TMS can be synthesized, for example, as taught in U.S. Pat. No. 5,137,919; Igarashi et al., J. Biol. Chem., 265, 5385, 1990; and Garmer et al., J. Org. Chem., 52, 2361, 1987.

Key portions of the TMS molecule have been identified. Those key portions of TMS have an effect on one or more of the activities set forth hereinabove. Various modifications can be made at such key sites to enhance a specific activity or several activities. For example, the D-erythro configuration at carbons 2 and 3 (numbering beginning from that side of the molecule bearing the nitrogen) is preferred over the D-threo, L-threo and L-erythro configurations. The impact of the 3 hydroxyl group can be mimicked by a compound carrying a functional group, such as a halogen, at the 5 position, as found in 5F-TMS.

The trimethyl substitution at the amine group is another critical portion of the TMS molecule. The methyl group of TMS effects the electron configuration of the positively charged nitrogen. Hence, other suitable groups, including hydrophobic groups, such as alkyl groups, can be substituted for the methyl group so long as the cationic character of the nitrogen atom is maintained. Thus, for example, one or more of the methyl groups can be replaced by a hydrocarbon group, such as, an aliphatic hydrocarbon, for example, an ethyl group, a propyl group, a butyl group, a pentyl group, a hexyl group and the like.

The parent TMS molecule carries a double bond at the $C_4$ position. While presence of the double bond is not essential for inhibition of protein kinase C (PKC or PK-C) activity, the particular steric configuration provided by the $C_4$ double bond does have an impact on inhibition of metastasis and platelet aggregation. A triple bond at $C_4$ is effective for inhibition of PKC but not for metastasis inhibition. Accordingly, the positioning of the one or more double bonds has a bearing on one or several TMS activities.

In concert with the number and positioning of double bonds, the size of and configuration of the aliphatic backbone can have a role in the TMS activities disclosed herein. Hence, the aliphatic chain may be a single chain, a branched chain or two chains may derive from the $C_4$ position.

Preferably, the aliphatic chain is non-polar or hydrophobic as it is known that a carboxyl or an ester group at the terminus of the aliphatic chain destroys certain TMS activities.

Figure 2:
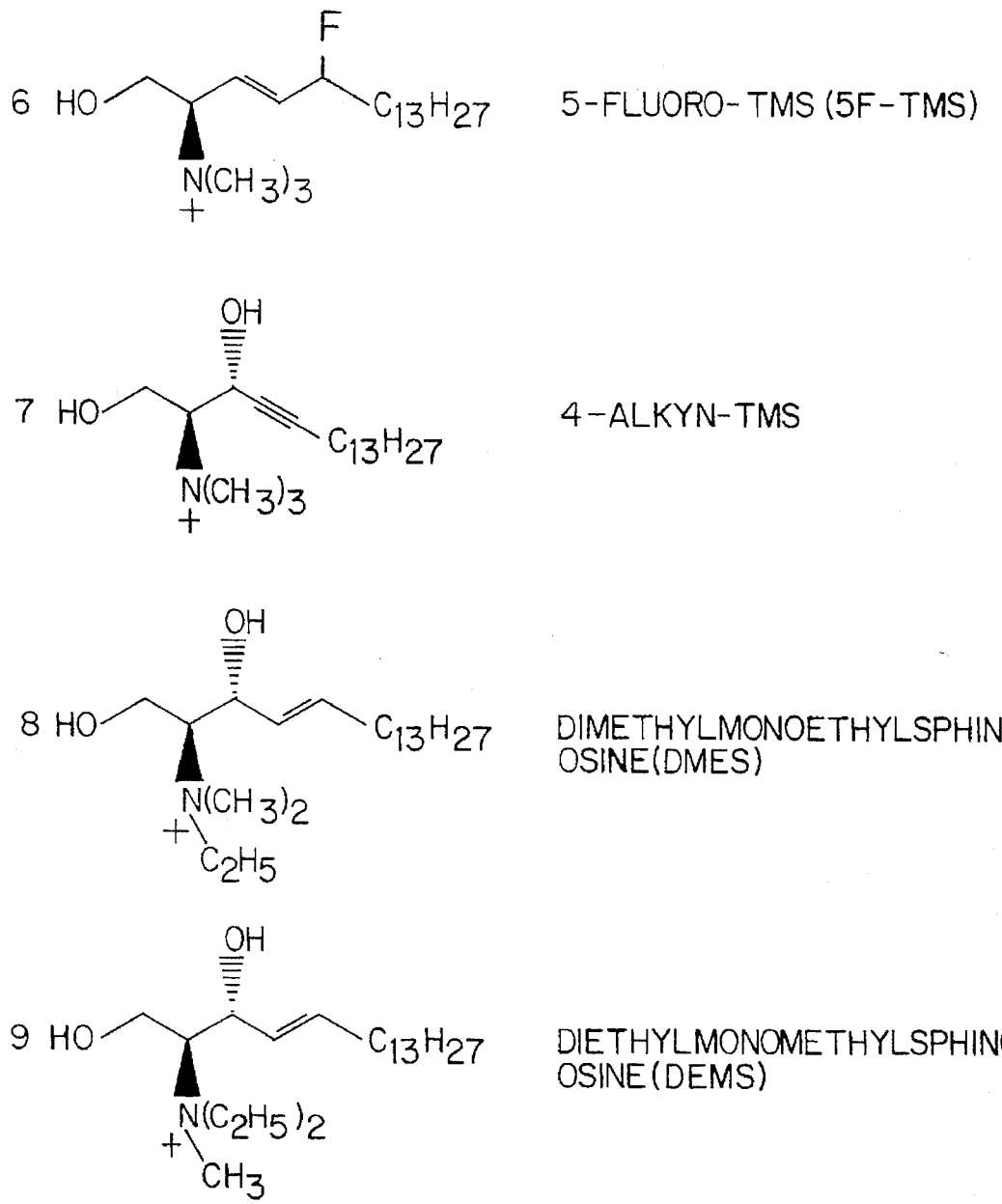
FIG. 2 depicts additional TMS derivatives.

Table I and FIGS. 1 and 2 set forth several TMS derivatives and activities thereof (Igarashi et al. J. Biol. Chem., 265, 5385, 1991), the data of which, in part, define key portions of the TMS molecule. Hence, removal of the double bond separates activities. A carboxyl or a methylester group at the terminus of the aliphatic chain and lack of the aliphatic chain destroy certain TMS activities.

Various modifications can be made to the TMS molecule to obtain derivatives which substantially retain one or more TMS activities. Any such derivatives are contemplated to fall within the scope of the instant invention. Of particular interest are those derivatives that retain only a portion of the parent activities or have enhanced activities.

Some modifications can affect other properties, that is not one of the specific TMS activities described herein, of the molecule, such as enhancing serum half-life, enhancing solubility in aqueous media, enhancing stability of the compound, reducing certain side effects, enhancing cellular permeability and the like. Hence, other derivatives may present more desirable use characteristics that are directed to subsidiary characteristics and properties.

The TMS derivatives of the instant invention can be made by known processes of organic synthesis based on and beginning with, for example, the synthetic scheme of TMS set forth in U.S. Pat. No. 5,137,919 and directed to those key portions of the

TABLE I

Effects of TMS derivatives
on metastasis of B16BL6 melanoma cells

| TMS Derivative | Inhibition of metastasis | Inhibition of PA | PKC inhibition |
| --- | --- | --- | --- |
| TMS | +++[1] | +++ | +++ |
| DHTMS | +[2] | ++ | +++ |
| Carboxy TMS | −[3] | − | − |
| Methylcarboxy TMS | −[3] | − | − |
| NTPS | −[3] | − | − |
| 5F-TMS | +++ | +++ | +++ |
| 4-alkyn-TMS | + | ++ | +++ |

[1]Free derivative and liposomal formulation were used
[2]Liposomal formulation was used
[3]Pre-incubation with free derivative
+ graded effectiveness
− not effective
PA platelet activation
PKC protein kinase C TMS molecule to enhance or to isolate activities or to other portions of the TMS molecule to enhance subsidiary characteristics or to remove unwanted subsidiary characteristics.

For example, DHTMS can be prepared by a synthetic scheme for making TMS except that the starting material is dihydrosphingosine, which is available commercially, for example, from Sigma.

NTPS can be obtained from phenylserine (Sigma) by the procedure described by Sommer et al. (J. Org. Chem., 36, 824, 1971).

Figure 3:
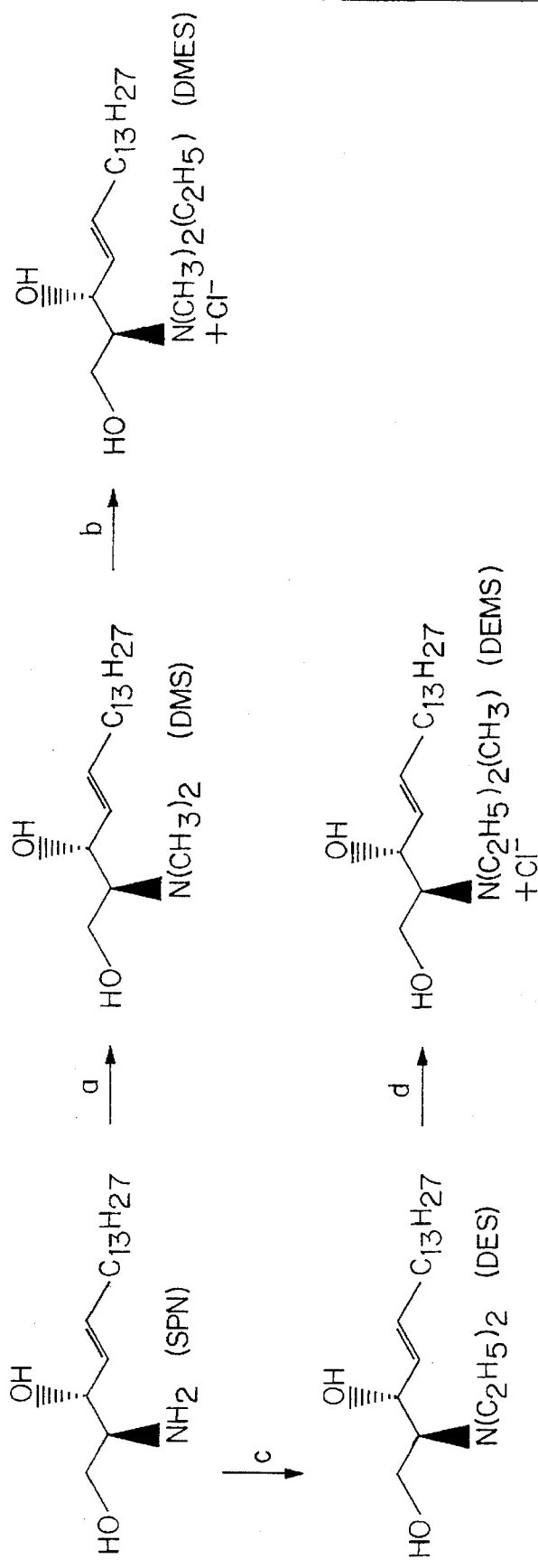
FIG. 3 depicts a synthetic scheme for making DMES and DEMS.
Figure 4:
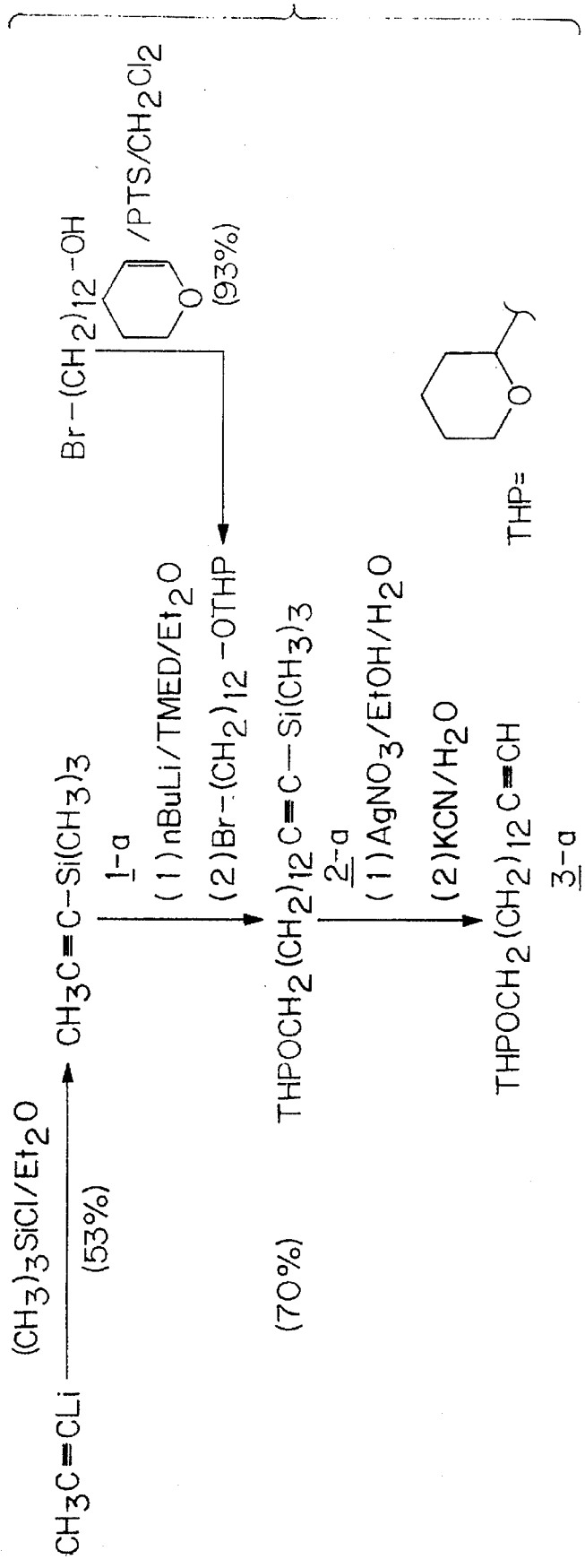
FIGS. 4-6 depict a synthetic scheme for making carboxy TMS and methylcarboxy TMS.
Figure 5:
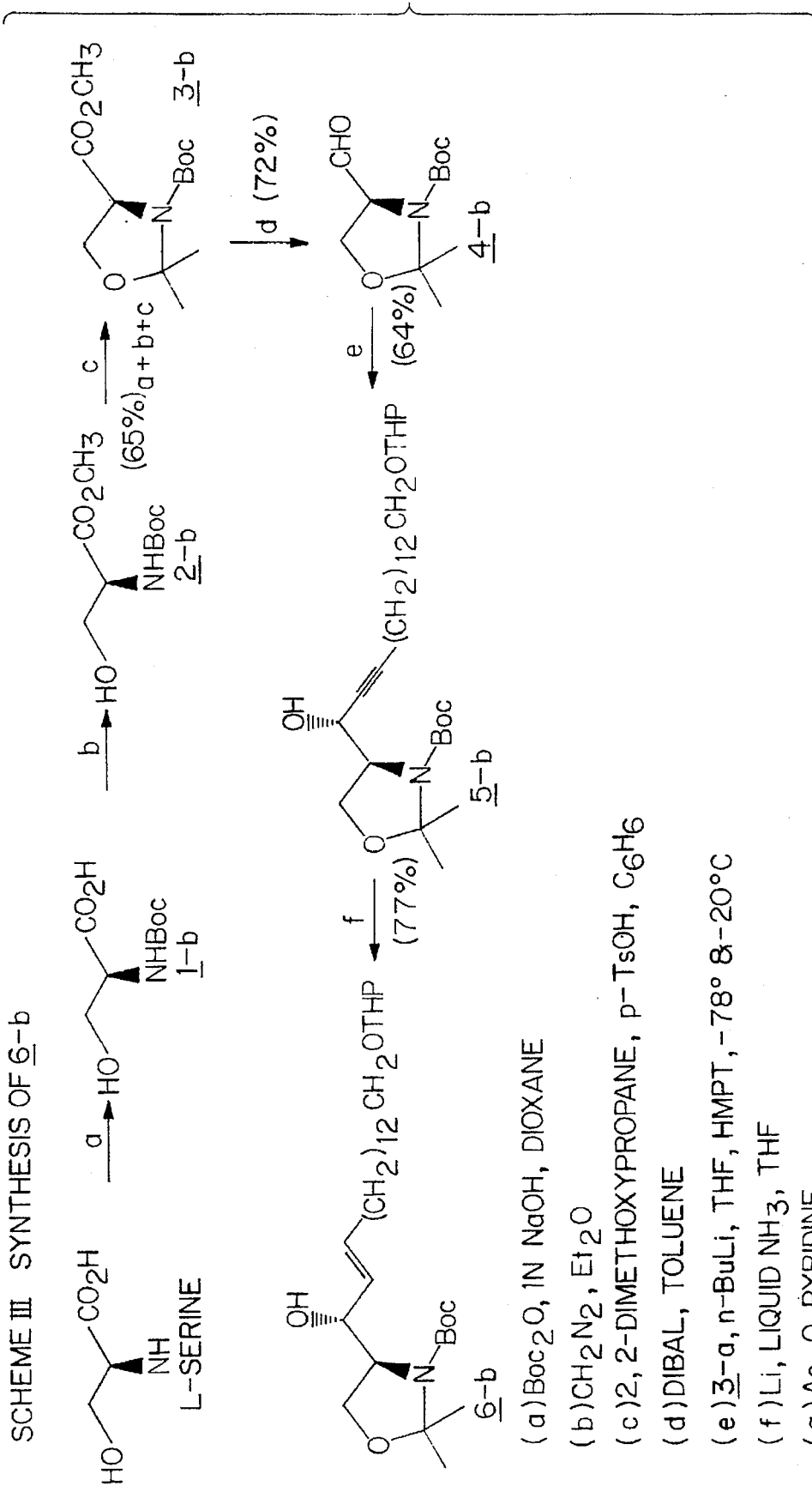
Figure 6:
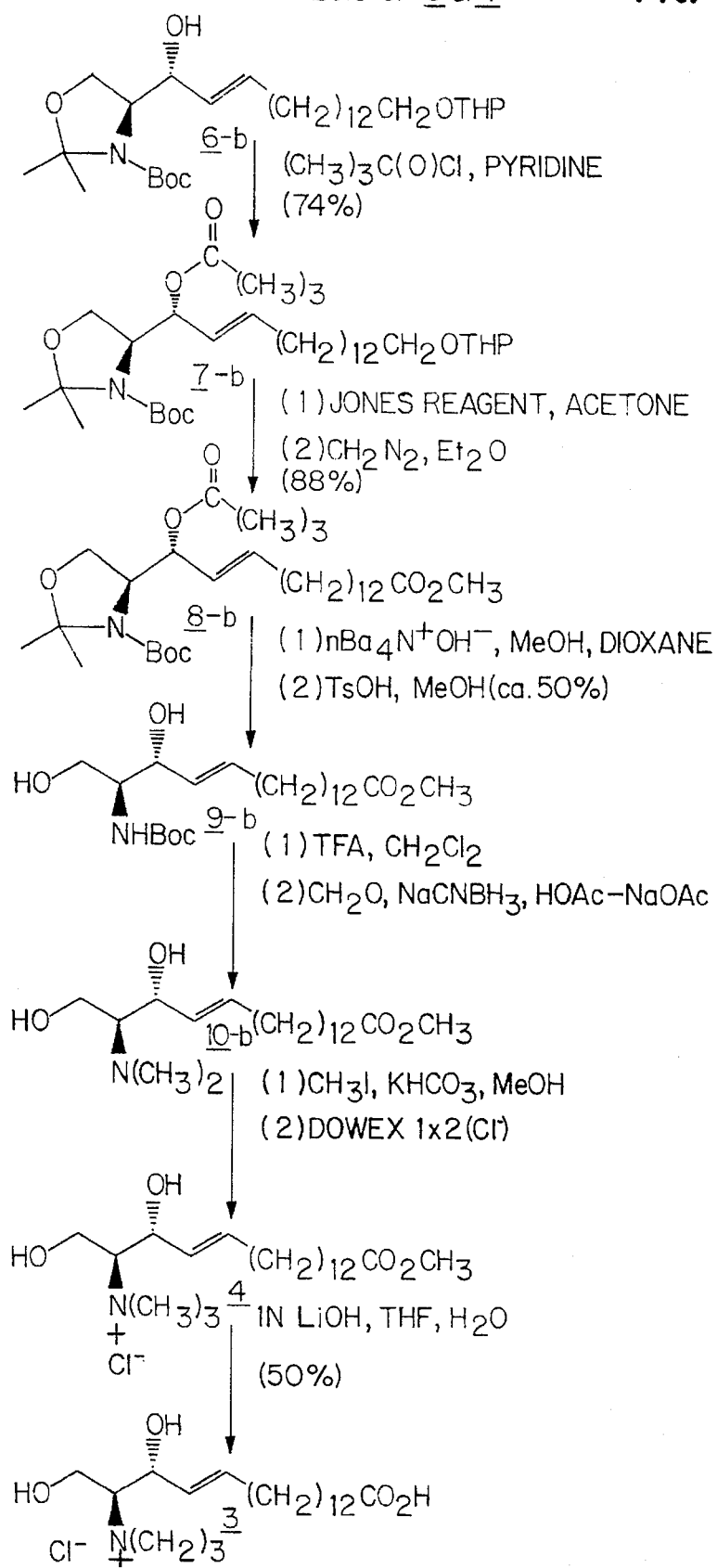
Figure 7:
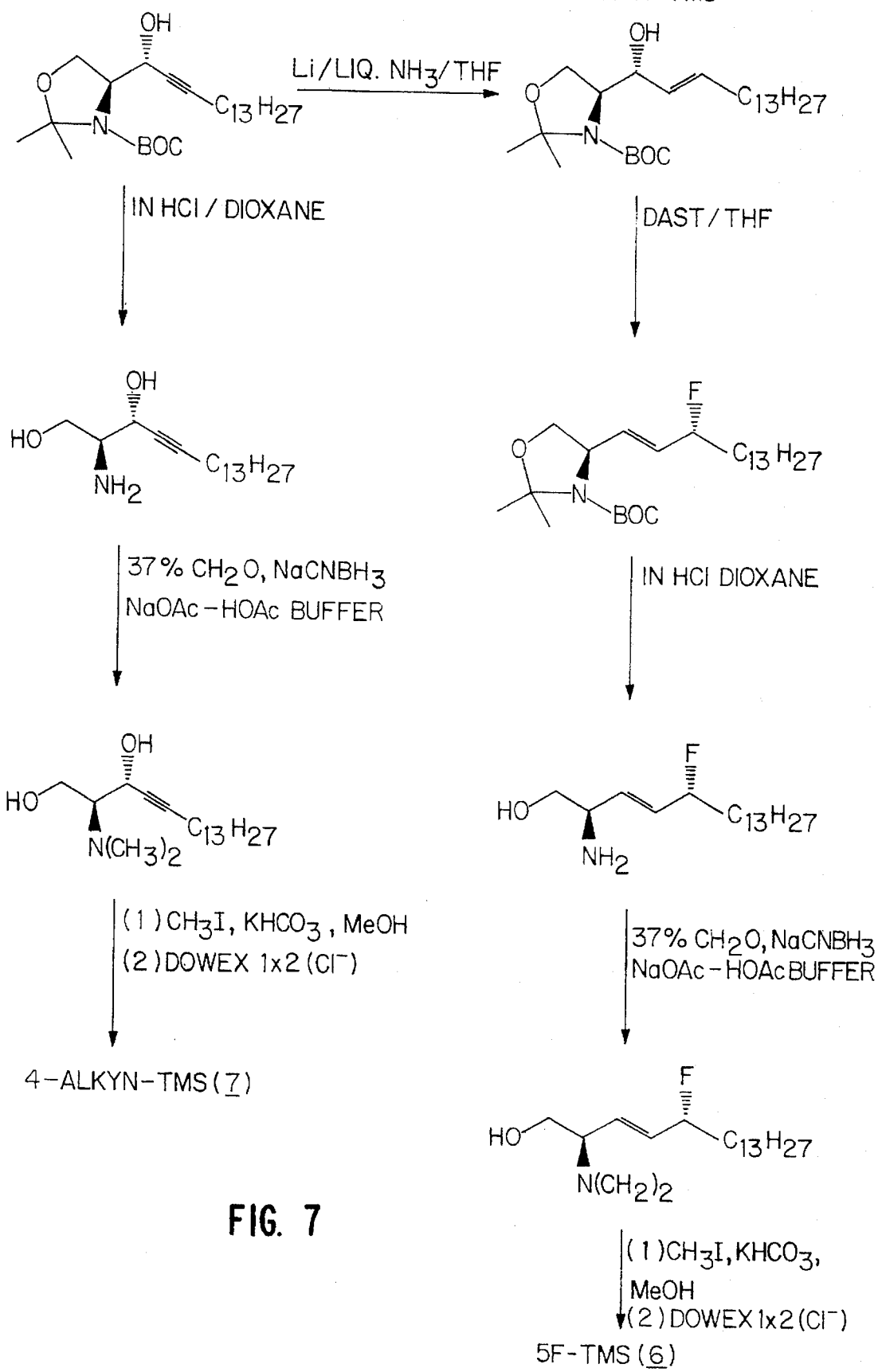
FIG. 7 sets forth synthetic schemes for making 5F-TMS and 4-alkyn-TMS.
Figure 8:
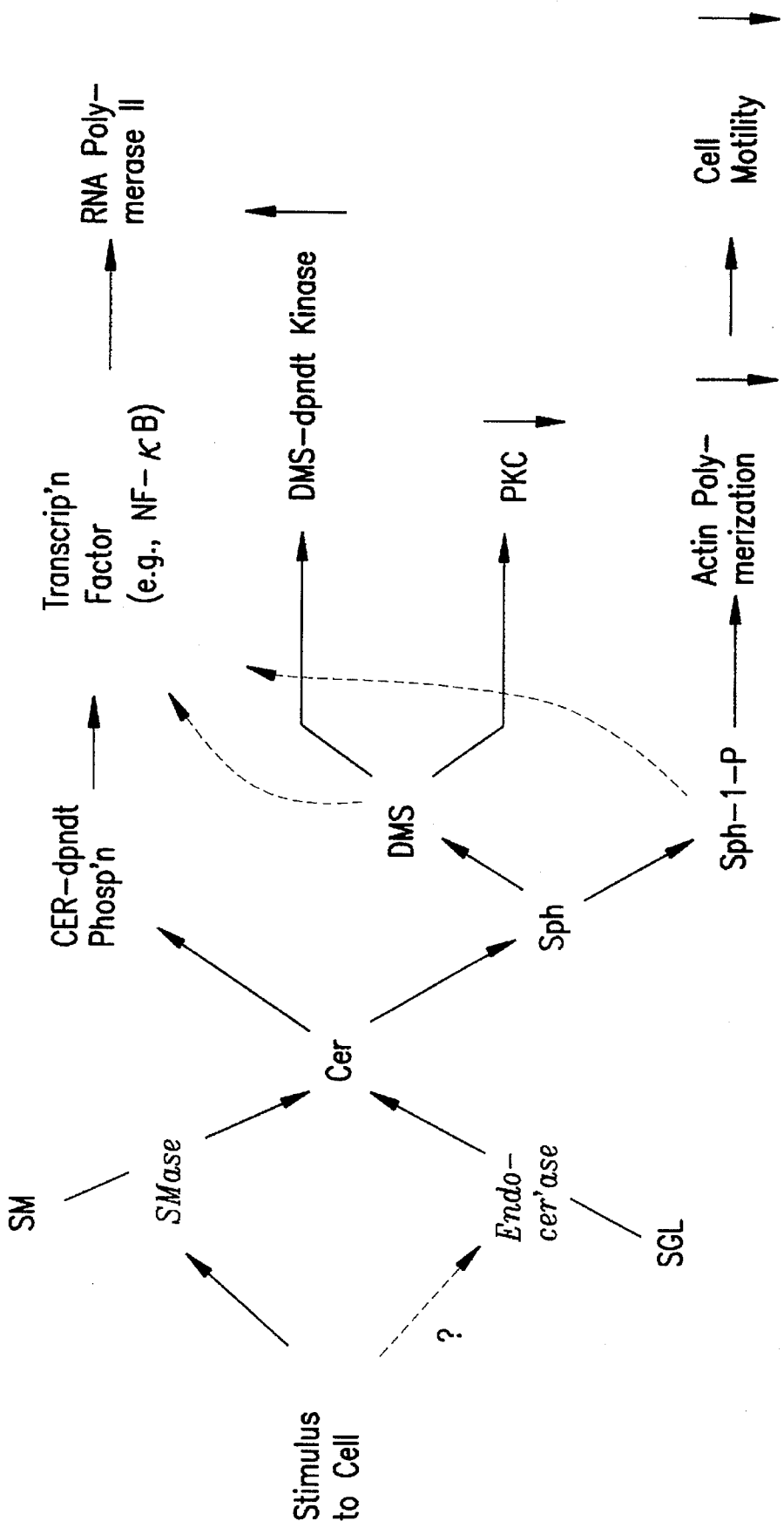
FIG. 8 illustrates the functional role of TMS and Sph-1-P derivatives. In the figure SM is sphingomyelin, Sgl is sphingolipid, Cer is ceramide, Sph is sphingosine, DMS is N,N-dimethylsphingosine, dpndt is dependent, transcrip'n is transcription, SMase is sphingomyelinase, cer'ase is ceramidase and phosp'n is phosphorylation. The noted transcription factor acts through RNA polymerase II.

A synthetic scheme for DMES and DEMS is set forth in FIG. 3. N,N-diethylsphingosine was prepared in a fashion similar to the synthesis of dimethylsphingosine. DEMS and DMES can be obtained by the treatment of diethylsphingosine with $CH_3I$ and dimethylsphingosine with $C_2H_5I$, respectively. The reaction conditions are essentially the same as set forth as to TMS except that the reaction can be conducted at a higher temperature and over a longer period of time to obtain suitable yields.

Sph-1-P can be made, for example, as taught in U.S. Pat. No. 5,260,288. The various Sph-1-P derivatives described therein may be used in the practice of the instant invention.

Sph-1-P and TMS are combinable in any of a variety of ratios, on a weight basis. Either of the active agents can predominate in the final composition or the agents can be present in equal amounts.

It is preferred to obtain potentiation of TMS activities. Generally, potentiation of TMS is obtained by having more TMS than Sph-1-P in the composition. Hence, the ratios of Sph-1-P and TMS preferably are those which enable the final composition to have a desirable level of TMS activity. For example, the ratio of TMS to Sph-1-P can be in the range of 1:1 to 50:1, preferably 1:1 to 40:1, more preferably 1:1 to 30:1 and even more preferably 1:1 to 20:1. It is possible that the preferred range may be 1:1 to 10:1 or as low as 1:1 to 5:1 or 1:1 to 2:1.

It is contemplated, however, because of the divergent activities of the two active agents, that the instant composition can contain more Sph-1-P than TMS to obtain other desired end activities. Hence, the amount of Sph-1-P to TMS in the final composition, on a weight basis, can be in the range of 1:1 to 50:1, preferably 1:1 to 40:1, more preferably 1:1 to 30:1 and even more preferably 1:1 to 20:1. It is possible that the preferred range may be 1:1 to 10:1 or as low as 1:1 to 5:1 or 1:1 to 2:1.

A medicament according to the instant invention is applicable both for in vitro and in vivo applications. Specific uses include treatment of malignancies, benign tumorous growths, inflammation, other manifestations of immune system dysfunction and when the immune system inappropriately or excessively responds to a stimulus.

The medicament comprises an effective amount of TMS and of Sph-1-P and a pharmaceutically acceptable carrier, diluent or excipient. The effective amount of TMS and of Sph-1-P can be determined using art-recognized methods, such as by establishing dose-response curves in suitable animal models, such as described herein or in non-human primates, and extrapolating to human; extrapolating from suitable in vitro data, for example, as described herein; or by determining effectiveness in clinical trials. Guidance can be obtained from the references cited herein.

Suitable doses of medicaments of the instant invention depend upon the particular medical application, such as the severity of the disease, the weight of the individual, age of the individual half-life in circulation etc., and can be determined readily by the skilled artisan. The number of doses, daily dosage and course of treatment may vary from individual to individual.

The instant composition can be administered in a variety of ways such as orally, parenterally and topically. Suitable pharmaceutically acceptable carriers, diluents, or excipients for the medicaments of the instant invention depend upon the particular medical use of the medicament and can be determined readily by the skilled artisan. Also, the instant composition can be delivered encapsulated within microspheres, such as liposomes, which can be made of phosphatidylcholine and cholesterol. The making and using of liposomes are known in the art. The use of liposomes is desirable from the standpoint that both active agents can be released at a specific site.

The medicament can take a variety of forms such as tablets, capsules, bulk or unit dose powders or granules; may be contained within liposomes; or may be formulated into solutions, emulsions, suspensions, ointments, pastes, creams, gels, foams or jellies. Parenteral dosage forms include solutions, suspensions and the like. The medicament is likely to contain any of a variety of art-recognized excipients, diluents, fillers etc. Such subsidiary ingredients include disintegrants, binders, lubricants, surfactants, emulsifiers, buffers, moisturizers, solubilizers and preservatives. The artisan can configure the appropriate formulation comprising the instant composition seeking guidance from numerous authorities and references such as, "Goodman & Gilman's, The Pharmaceutical Basis of Therapeutics" (6th ed., Goodman et al., eds., MacMillan Publ. Co., NY, 1980).

In body sites that are characterized by continual cell growth or require cell growth inhibition because of dysfunction and are relatively inaccessible, the instant composition can be administered in a suitable fashion to assure effective local concentrations. For example, the instant composition may be injected in a depot or adjuvant, carried in a surgically situated implant or reservoir that slowly releases a fixed amount of the instant composition over a period of time or may be complexed to recognition molecules with the capability of binding to the site presenting with abnormal cell growth. An example of such a contemplated scenario is a recognition molecule that is an antibody with binding specificity for a bone marrow specific antigen wherein said marrow specific antibody is complexed to and the antigen binding sites thereof are exposed at the surface of a liposome carrying the instant composition there within, said complex administered to a patient with leukemia.

It is preferred that the composition to be administered to an animal be encapsulated in an inert material to provide a delivery form which minimizes any local side effects. For example, the instant combination can be encased in microcapsules or microspheres, such as the so-called, "time release capsules", of over-the-counter pharmaceuticals, such as CONTACT®.

Alternatively, the instant composition can be encapsulated within biological-type microcapsule and microspheres, such as, liposomes or vesicles, for example, those which contain a lipid, membrane-like limiting layer. Various lipids can be used to generate liposomes with characteristics of the final product dependent thereon.

Accordingly, TMS, or derivatives thereof, and Sph-1-P, or derivatives thereof, or biologically acceptable salts thereof, suspended in the desired ratio in an aqueous medium are added to a vessel containing appropriate amounts of membrane forming lipids, such as phosphatidylcholine and cholesterol. The mixture is treated, for example, by sonication, to yield structures comprising an enclosing lipid membrane-like structure containing within the aqueous solution comprising the instant composition of TMS and Sph-1-P.

For example, egg phosphatidylcholine, cholesterol, TMS and Sph-1-P in a molar ratio of 4.5:4.5:1:0.1 are mixed, the mixture is evaporated and is treated to produce liposomes (Kraft & Anderson, Nature, 301, 621, 1983; Igarashi et al., Biochemistry, 28, 6796, 1989). In view of such a formulation, a single administration of the instant composition according to the above-noted formulation can consist of 0.25 mg of TMS and 0.025 mg of Sph-1-P.

As an example, mice were injected subcutaneously with the metastatic and invasive BL6 cell line (Hart et al., Amer. J. Path., 97, 587, 1979; Poote et al., Canc. Res., 42, 2770, 1982) ($1\times10^5$ cells in 0.05 ml of Dulbecco-modified Eagle's medium). A single intravenous injection of the 10:1 liposomal TMS/Sph-1-P composition described hereinabove was administered on days 5, 10, 15, 20, 25 and 30. The primary tumor was excised on day 21 and lung colonization was assessed on day 35. Hence, tumor development in situ and metastasis and colony development can be assessed in that model. Controls comprised liposomes containing TMS alone, liposomes containing Sph-1-P alone, liposomes containing medium or medium alone with no liposomes.

Sph-1-P alone was no different in effect from medium alone or liposomes containing medium only. Lung colony number in mice receiving the instant composition was reduced greatly as compared to the medium control and to mice which had been injected with liposomes containing TMS but not Sph-1-P.

Hence, the instant composition can find utility in inhibiting tumor cell proliferation and tumor cell motility. TMS has an impact on kinase-dependent cell activities and Sph-1-P has an impact on actin filament reorganization. The instant composition is useful in view of the current view of metastasis wherein two separate cellular pathways are implicated, one of active autonomous cell proliferation by enhanced transmembrane signaling and the other by enhanced cell motility which promotes transendothelial migration and infiltration into tissue spaces.

The instant composition can find a variety of uses whenever cell growth and proliferation need to be controlled. Hence, the instant invention finds applicability to in vitro scenarios, such as tissue and organ culture.

For example, often valuable cell cultures and cell lines are contaminated by faster growing cells. A common contaminant of human cell cultures is the HeLa cell line. Hence, desired but contaminated cultures can be exposed to the instant composition to control the rampant growth of the contaminant cells. The instant composition can be used to treat contamination or be used prophylactically in a preventative or maintenance fashion.

The instant invention now will be exemplified by the following non-limiting examples.

EXAMPLE 1

Human lymphocyte cultures in RPMI-1640 medium containing 15% fetal calf serum and contaminated with HeLa cells are treated with varying amounts of composition comprising TMS and Sph-1-P in varying ratios, by weight, to ascertain an optimal amount for use. The ratios vary from 1:1, 1:2, 1:5, 1:10 through 1:20 of S-1-P to TMS. The amount of TMS used is in the 0–100 µM range. The optimal amount and ratio is assessed by finding samples with maximal inhibition of HeLa cell growth and a minimal effect on the viability and growth of the lymphocytes.

EXAMPLE 2

Tobacco protoplasts are prepared and cultured as described by Samac et al., Virol., 131:455–462 (1983). To the culture medium is added a prophylactic amount of TMS/Sph-1-P combination to control for contamination and promote growth of the fastidious tobacco protoplasts.

EXAMPLE 3

Human fibroblasts for use as feeder cells (ATCC CRL 1502) are maintained in Eagle's MEM with 10% FCS and a prophylactic amount of TMS/Sph-1-P combination. Thus, when the anchorage-dependent cells form confluent monolayers, the monolayers can be maintained with the above-noted media, optionally supplemented with antibiotics, to minimize the need for passing the cells and to lower the risk of contamination with faster growing cells, such as HeLa.

EXAMPLE 4

Figure 9A:
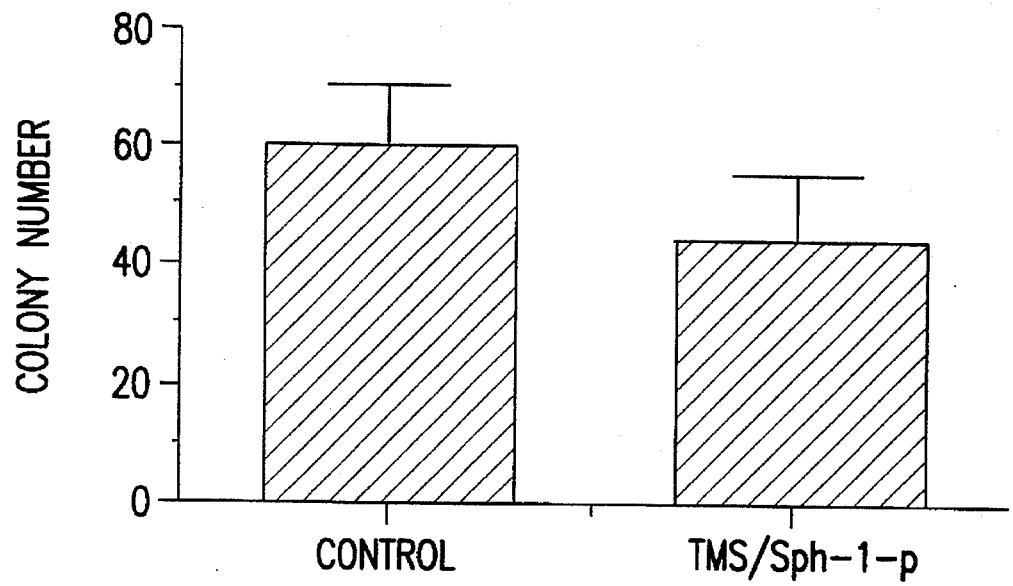
FIGS. 9A and 9B depict the effect of liposomes containing both TMS and Sph-1-P on tumor growth in a model of experimental metastasis (FIG. 9A) and in a model of spontaneous metastasis (FIG. 9B).
Figure 9B:
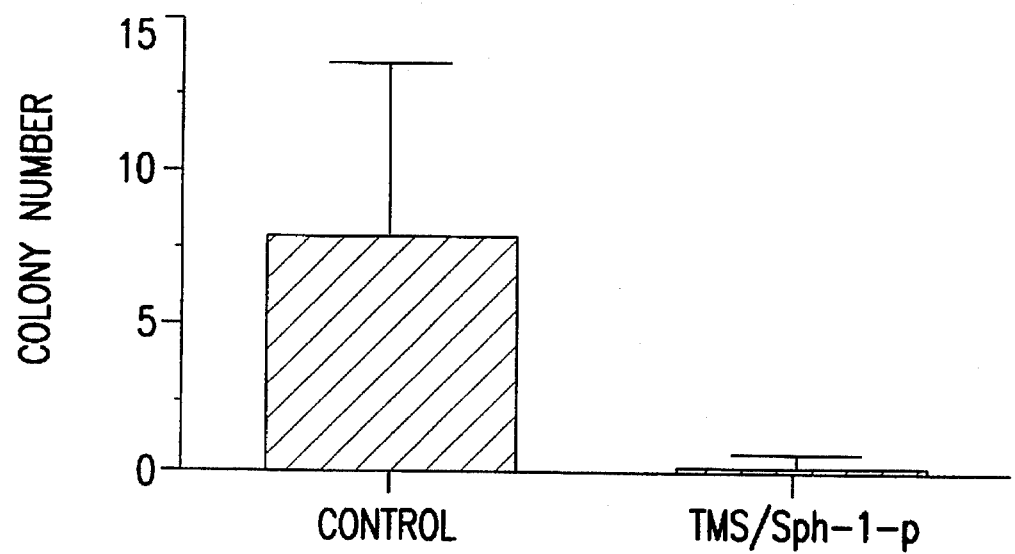

Models for experimental and spontaneous metastasis are used to demonstrate the activity of the instant composition. Experimental metastasis can be demonstrated by the intravenous injection of tumor cells followed by administration of the instant composition encapsulated in liposomes, see FIG. 9B.

Spontaneous metastasis can be demonstrated by the subcutaneous injection of tumor cells and the eventual development of a tumor at that injection site. Then the instant composition encapsulated in liposomes is administered to the hosts, see FIG. 9A.

In either model, the number of lung tumor colonies is ascertained macroscopically and microscopically following a course of repeated liposome administration.

Free TMS or TMS encapsulated in liposomes have a strong effect in the experimental metastasis model. However, as noted in FIG. 9A, the instant composition has a very slight effect in the experimental metastasis model. However, as noted in FIG. 9B, the instant composition has a profound effect in the spontaneous metastasis model.

All references cited herein are incorporated herein by reference.

While the invention has been described in detail and with reference to certain embodiments thereof, it would be apparent to one skilled in the art that various changes and modifications can be made without departing from the spirit and scope thereof.

What is claimed is:

1. A composition comprising N,N,N-trimethylsphingosine and sphingosine-1-phosphate in potentiate amounts.

2. The composition of claim 1, wherein said trimethylsphingosine and said sphingosine-1-phosphate are in a ratio of 1:1 to 50:1.

3. The composition of claim 2, wherein said ratio is 1:1 to 20:1.

4. The composition of claim 3, wherein said ratio is 10:1.

5. A liposome comprising the composition of claim 1.

* * * * *